United States Patent [19]

Cope et al.

[11] Patent Number: 5,294,436
[45] Date of Patent: Mar. 15, 1994

[54] METHOD OF HIGHLIGHTING HAIR AND COMPOSITION THEREFOR

[75] Inventors: Gary M. Cope, Texarkana, Tex.; Michael S. DeGeorge, Toms River, N.J.

[73] Assignee: Hairnetwork, Inc., Texarkana, Tex.

[21] Appl. No.: 935,826

[22] Filed: Aug. 26, 1992

Related U.S. Application Data

[63] Continuation-in-part of Ser. No. 823,888, Jan. 22, 1992, abandoned.

[51] Int. Cl.$^5$ .................. A61K 7/135; A61K 33/40
[52] U.S. Cl. .................................... 424/62; 132/208; 424/616; 424/DIG. 3
[58] Field of Search ............. 424/62, DIG. 3, 616; 132/202, 208

[56] References Cited

U.S. PATENT DOCUMENTS

| | | | |
|---|---|---|---|
| 3,726,967 | 4/1973 | Vorsatz | 424/DIG. 3 |
| 4,010,872 | 3/1977 | Lozano | 424/DIG. 3 |
| 4,114,632 | 9/1978 | Morganroth | 424/DIG. 3 |
| 4,170,637 | 10/1979 | Pum | 424/62 |
| 4,247,537 | 1/1981 | Lunn | 424/62 |
| 4,313,392 | 2/1982 | Watts | 424/DIG. 3 |
| 4,327,751 | 5/1982 | Evans | 424/62 |

*Primary Examiner*—Paul R. Michl
*Assistant Examiner*—Sally Gardner
*Attorney, Agent, or Firm*—William J. Scherback

[57] ABSTRACT

Human hair is highlighted by a procedure in which the hair initially is moistened with water and towel dried. The hair is then teased and on the teased hair is sprinkled a dry powder bleach mixture which sifts downward through the hair. A mist of a solution of hydrogen peroxide is applied to the dry powder bleach mixture and thereafter the hair is rinsed and shampooed. The final rinsing and shampoo takes place within five minutes following application of the solution of hydrogen peroxide. A dry solid powder composition used in the procedure includes at least one oxidizing agent, an activator to change the PH of the oxidizing agent from acidic to alkaline, a drying agent for absorbing moisture present in the mixture, an accelerator for accelerating the bleaching process, a thickening agent, a humectant and a chelate agent.

10 Claims, No Drawings

METHOD OF HIGHLIGHTING HAIR AND COMPOSITION THEREFOR

RELATED APPLICATIONS

This application is a continuation-in-part of application Ser. No. 07/823,888 filed Jan. 22, 1992, now abandoned.

BACKGROUND OF THE INVENTION

1. Field of the Invention

This invention relates to a new technique for treating human hair to effect what has become known in the art as highlighting together with a novel dry powder bleach composition activated by the application of hydrogen peroxide, preferably to be used with the technique.

2. Description of the Prior Art

Powder bleach materials are known in the hair coloring art which when mixed with a developer such as hydrogen peroxide of various strengths or volumes, can be applied to the hair as a bleach.

A common practice in salons providing hair highlighting and hair frosting is to cover the hair with a plastic cap having numerous perforations through which tufts of hair are pulled for treatment. A dry powder bleach composition is then mixed with hydrogen peroxide to form a paste. Protected by plastic gloves the operator then applies the paste to the tufts of hair extending through the perforations in the plastic cap. This process which leaves lightened streaks in the hair, and usually changes the color of the hair, typically takes from 35 to 45 minutes. Because the paste is uniformly rubbed into the hair down to the base of the plastic cap there is a finite line of demarcation between the treated and the untreated hair. As the hair grows out, the untreated hair or roots become obvious necessitating rather frequent retreatment of the process.

The highlighting or bleaching of hair requires a highlight or bleach composition typically activated by a mixture with hydrogen peroxide of different volumes or strengths. These compositions are mixed with hydrogen peroxide to provide the paste applied to the hair. There are many such compositions on the market today suitable for use with the tedious process above described. There obviously is a need for a faster, less time-consuming technique for highlighting human hair and for a dry powder composition which enables the process. Those needs are met by the present invention which has as an object a new and improved technique for highlighting human hair which is significantly less time-consuming than those previously employed.

It is another object of the present invention to provide a dry powder composition which remains stable and is freely disbursible and which when activated by hydrogen peroxide will rapidly effect the highlighting of human hair.

SUMMARY OF THE INVENTION

In accordance with the present invention a method of highlighting the natural color of human hair begins with the initial step of moistening the hair with water and towel drying it. The hair is then teased lightly and thereafter there is sprinkled a dry powder bleach mixture uniformly onto the hair permitting some of the mixture to sift downward through the hair toward the scalp. A mist of a solution of hydrogen peroxide is then applied to the hair and to the mixture. A reaction takes place between the hydrogen peroxide and the dry powder bleach mixture immediately to begin highlighting the hair strands. In addition, where the hydrogen peroxide hits the hair alone one obtains a different shade of highlighting. And where the strands of hair are not contacted with hydrogen peroxide there is no change. The overall effect is that of closely related blends along the lengths of the hair strands to produce an overall lighter blend of color. After a period of time not to exceed five (5) minutes following the application of hydrogen peroxide the hair is rinsed with water and shampooed.

The strength of the aqueous solution of hydrogen peroxide is in the range of 30 to 50 volume. The selected strength is a function of the degree or level of highlighting to take place.

A suitable dry powder bleach mixture is a composition comprised of at least one oxidizing agent, an activator to change the PH of the oxidizing agent from acidic to alkaline, a drying agent for absorbing moisture present in the mixture, an accelerator for accelerating the bleaching process, and a thickening agent. A chelate agent will be desirable for use in geographical areas where iron is present in the water supply. A humectant may be added for hair conditioning purposes. Coloring agents, for coding purposes, may also be added both to the composition and to the aqueous solution of hydrogen peroxide.

If after examining the appearance of the highlighting procedure it is determined that further highlighting may be desired, the process is repeated and additional amounts of dry powder bleach sprinkled uniformly onto the hair, the hair sprayed with hydrogen peroxide and the hair rinsed and shampooed within a period not to exceed two minutes following the application of hydrogen peroxide.

DESCRIPTION OF A PREFERRED EMBODIMENT

In carrying out the method of the present invention to highlight strands of human hair, the hair of the customer or patron is initially moistened with water and towel dried. The towel dried hair is then teased lightly along the lengths near the ends and more heavily toward the base of the hair strands in effect to provide a more dense mass to protect the scalp from the materials to be used in order further to separate the hair strands and to provide rough surfaces on which powder particles more readily may adhere. A dry powder composition or mixture is now sprinkled onto the hair using any convenient device similar to a salt shaker or a flour sifter. The powder particles adhere to the roughened surfaces of the hair strands. Care should be exercised to assure a uniform distribution of the mixture. Should an excessive amount of the composition inadvertently be placed in one location in the hair, the operator can use his or her hand, preferably protected by a plastic glove, to distribute the composition to provide for uniformity. The dry composition will naturally fall through the hair toward the scalp of the patron, but kept from the scalp by the heavier teasing, resulting in a variation in the density of the composition ranging from a minimum near the scalp to a maximum near the ends of the hair strands. The intent is to provide a gradual highlighting of the hair strands and thus avoid the sharp lines of demarcation that result from the technique of the prior art wherein strands of hair are pulled through holes in a plastic cap and the bleaching mud or paste uniformly applied along the length of the exposed hair strands.

With the powder bleach composition in place, there is now applied a fine mist of a solution of hydrogen peroxide to the hair and thus to the particles of the dry powder bleach composition. A reaction takes place, a bleaching effect highlighting the strands of hair. The degree of highlighting varies along the length of the hair strands with the maximum level occurring at the places where particles of the composition are present and are contacted by the hydrogen peroxide. Following the application of the solution of hydrogen peroxide and not more than five (5) minutes following the initial application of the hydrogen peroxide, the hair is rinsed and shampooed.

Upon examination, should the patron decide that the highlighting was inadequate, the procedure may be repeated. Specifically, additional amounts of dry powder bleach composition are again sifted onto the hair and then misted or sprayed with the hydrogen peroxide. However, this time the hair will be rinsed and shampooed after no more than two minutes following the application of the hydrogen peroxide.

The overall result is quite pleasing and the overall procedure is accomplished in short order. A significantly shorter period of time is involved in the practice of the present invention than in the practice of the prior art. There is no need laboriously to pull strands of hair through holes in a plastic skull cap and thereafter covering the exposed strands of hair one group at a time with a bleaching mud or paste.

In carrying out the method of the present invention, the client or patron should be protected from the bleaching composition and from the hydrogen peroxide. Specifically, the client or patron should be properly covered with a water repellant cape and a towel placed securely around the neck. A moisture cream or petroleum jelly should be applied around the hairline, the top of the ears, behind the ears and around the neckline. An additional towel can be used by the client or patron to be draped over the hands and held up to the hairline at the forehead in order to protect the hands and the eyes. This protective procedure is strongly recommended in view of the fact that the powder composition is sifted freely over the hair and the aqueous solution of hydrogen peroxide is applied by spritzing or spraying over the hair. These products may, through inadvertence, be scattered upon the person of the client or patron, thus dictating the aforementioned protective measures.

Depending upon the degree or level of highlighting desired by the client or patron, the strength of the aqueous solution of hydrogen peroxide may vary in the range of 30 to 50 volume. The strength of the aqueous solution of hydrogen peroxide may readily be identified by the use of water soluble dyes such for example as FD&C Red #4, FD&C Yellow #5 or C.I. Basic Blue 99.

A dry powder bleach composition suitable for use in the practice of the above described method is comprised of at least one oxidizing agent, an activator to change the PH of the oxidizing agent from acidic to alkaline, a drying agent for absorbing moisture that might be present in the mixture, an accelerator for accelerating the bleaching process, and a thickening agent to enhance the adherent properties of the composition to the strands of hair. A humectant may be added for hair conditioning purposes. A chelate agent will be desirable for use in geographical areas where iron is present in the water supply. The oxidizing agent may be selected from the class consisting of potassium persulfate, ammonium persulfate and sodium persulfate. The activator may be selected from the class consisting of sodium metasilicte, lithium silicate, sodium silicate and magnesium oxide. The drying agent may be selected from the class consisting of silica, hydrated silica, aluminum stearate and magnesium stearate. The accelerator may be selected from the class consisting of magnesium oxide. The thickening agent or rheology modifier may be selected from the class consisting of ethyl hydroxyethyl cellulose, methyl cellulose, carboxymethyl hydroxyethyl cellulose, cellulose gum and hydroxypropyl cellulose. The amount of thickening agent used is insufficient to make a paste of the composition. The humectant may be selected from the class consisting of sorbitol, mannital, sucrose and xylitol. To protect the composition from ferrous contamination a chelate agent is added, selected from the class consisting of disodium EDTA, trisodium EDTA and tetrasodium EDTA.

Finally, it may be desirable to include a coloring agent with the dry powder mixtures to relate them to the selected strength of the aqueous solution of hydrogen peroxide. The function provided by a coloring agent added to the dry powder composition is merely for marketing purposes where it is intended to package the hydrogen peroxide and the dry powder composition and sell them as units. As in the case of the coloring agents for the aqueous solution of hydrogen peroxide, coloring agents are added to the composition which agents are referred to generally as color coding material. These would include red D&C 30, yellow D&C 10 and ultramarine blue.

A preferred dry powder bleach composition will include two oxidizing agents, potassium persulfate and ammonium persulfate which have different degrees of bleaching characteristic, one being faster than the other with the combination of the two giving a control over the hair lightening process. The ammonium persulfate acts upon the hair strands to facilitate the entry of the hydrogen peroxide onto the strands of hair. The action is quite harsh and therefore the amount of ammonium persulfate should be minimized to avoid damaging the hair. But there exists a need for oxygen in the process and this is provided by the potassium persulfate.

The composition further may include a conditioner selected from the class consisting of sodium stearate and potassium stearate.

The preferred composition of the dry powder bleach mixture includes the following materials: Potassium Persulfate, Ammonium Persulfate, Sodium Metasilicate, Sodium Stearate, Fumed Silica (Aerosil 200), Aluminum Stearate, Magnesium Oxide, Disodium EDTA, Hydroxyethyl Cellulose FQ481, Sorbitol, and the color coding material.

Specifics of a composition, which has been found to be useful in the practice of the hair highlighting technique, are set forth below in Table A.

TABLE A

| | |
|---|---|
| Potassium Persulfate | 40.2975% |
| Ammonium Persulfate | 19.9000% |
| Sodium Metasilicate | 12.9350% |
| Sodium Stearate | 11.9400% |
| Fumed Silica (Aerosil 200) | 5.9700% |
| Aluminum Stearate | 2.9850% |
| Magnesium Oxide | 1.9900% |
| Disodium EDTA | 1.4925% |
| Hydroxyethyl Cellulose FQ481 | 0.9950% |
| Sorbitol | 0.9950% |

TABLE A-continued

| | |
|---|---|
| Color Coding Material | 0.5000% |

The concentration of thickening agent, hydroxyethyl cellulose FQ481, in the preferred composition is sufficient to enhance the adherence of the composition to the strands of hair but inadequate to form a paste when the composition is mixed with hydrogen peroxide.

Ranges of concentration of thickening agents which provide the desirable property of causing the composition to adhere to the strands of hair while avoiding the formation of a paste when the composition is contacted or mised with hydrogen peroxide are set forth below in Table B.

TABLE B

| Thickener | Range |
|---|---|
| Ethyl hydroxyethly cellulose FQ481 | 0.5%–1.0% |
| Methyl cellulose | 0.5%–1.0% |
| Carboxymethyl hydroxyethyl cellulose | 0.1%–0.5% |
| Cellulose gum | 0.1%–0.5% |
| Hydroxypropyl cellulose | 0.3%–0.6% |

To accommodate the above ranges, the concentraion of Sorbitol can be varied to bring the formulations to 100%.

Now that the invention has been described in detail, modifications will suggest themselves to those skilled in the art and it is intended that such modifications be included within the scope of the appended claims.

We claim:

1. The method of highlighting the natural color of human hair comprising the steps of
   a. moistening the hair with water and towel drying it,
   b. teasing the hair lightly,
   c. sprinkling a dry powder bleach mixture uniformly onto the hair permitting some of the mixture to sift downward through the hair, said bleach mixture comprising at least one oxidizing agent, an activator to change the pH of the oxidizing agent from acidic to alkaline, a drying agent for absorbing moisture present in the mixture, and a thickening agent,
   d. applying a mist of a solution of hydrogen peroxide to the hair to contact the mixture, said hydrogen peroxide having a strength in the range of 30 to 50 volume, and
   e. rinsing and shampooing the hair within five (5) minutes after application of the hydrogen peroxide.

2. The method of claim 1 in which a protective cream is applied around the hair line, top of the ears and around the neck line prior to sprinkling of the dry powder bleach mixture.

3. The method of claim 1 in which care is exercised in the sprinkling step to avoid contact of the bleach mixture with the scalp.

4. The method of claim 1 in which the strength of the solution hydrogen peroxide is color coded.

5. The method of claim 1 in which the dry powder bleach mixture is a composition comprised of
   at least one oxidizing agent,
   an activator to change the PH of the oxidizing agent from acidic to alkaline,
   a drying agent for absorbing moisture present in the mixture, and
   an accelerator for accelerating the bleaching process.

6. The method of highlighting the natural colors of human hair comprising repeating steps c. and d. of claim 1, and rinsing and shampooing the hair within two (2) minutes following the application of hydrogen peroxide.

7. The method of claim 1 in which the bleach mixture also includes a chelating agent.

8. The method of claim 1 in which the bleach mixture further includes a humectant.

9. The method of claim 1 in which the bleach mixture further includes a chelating agent and a humectent.

10. The method of claim 1 in which said thickening agent is present in amount to enhance adherence of the mixture to strands of hair but insufficient to enable the mixture to be formed into a paste.

* * * * *